: US 6,210,301 B1
(12) United States Patent
Abraham-Fuchs et al.

(10) Patent No.: US 6,210,301 B1
(45) Date of Patent: Apr. 3, 2001

(54) PATIENT MONITORING SYSTEM

(75) Inventors: Klaus Abraham-Fuchs, Erlangen; Thomas Birkhoelzer, Welsendorf; Alexander Herold, Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/355,065

(22) PCT Filed: Jan. 21, 1998

(86) PCT No.: PCT/DE98/00175

§ 371 Date: Sep. 9, 1999

§ 102(e) Date: Sep. 9, 1999

(87) PCT Pub. No.: WO98/32497

PCT Pub. Date: Jul. 30, 1998

(30) Foreign Application Priority Data

Jan. 22, 1997 (DE) .............................................. 197 02 150

(51) Int. Cl.⁷ .................................................. A63B 21/00
(52) U.S. Cl. .................................. 482/8; 482/51; 601/23
(58) Field of Search ................................. 482/1–9, 51, 66, 482/900–903; 601/5, 23, 40, 33–35

(56) References Cited

U.S. PATENT DOCUMENTS

| 5,538,486 | 7/1996 | France et al. . |
| 5,715,160 | * 2/1998 | Plotke ................................. 482/900 |
| 5,716,330 | * 2/1998 | Goldman ............................... 482/51 |

FOREIGN PATENT DOCUMENTS

| 32 09 850 | 3/1985 | (DE) . |
| 40 39 648 | 7/1992 | (DE) . |
| WO 91/012786 | 9/1991 | (WO) . |

* cited by examiner

Primary Examiner—Glenn E. Richmon
(74) Attorney, Agent, or Firm—Schiff Hardin & Waite

(57) ABSTRACT

A patient monitoring system, particularly for orthopedics, is designed for use by the medical layman and provides this person with information relating to the exercises or activities he performs. To this end, a sensor array produces sensor signals which are stored in a first memory and are compared to the contents of a second memory (ideal signal pattern). The comparison result is made available to the user via a display or as a biofeedback.

7 Claims, 1 Drawing Sheet

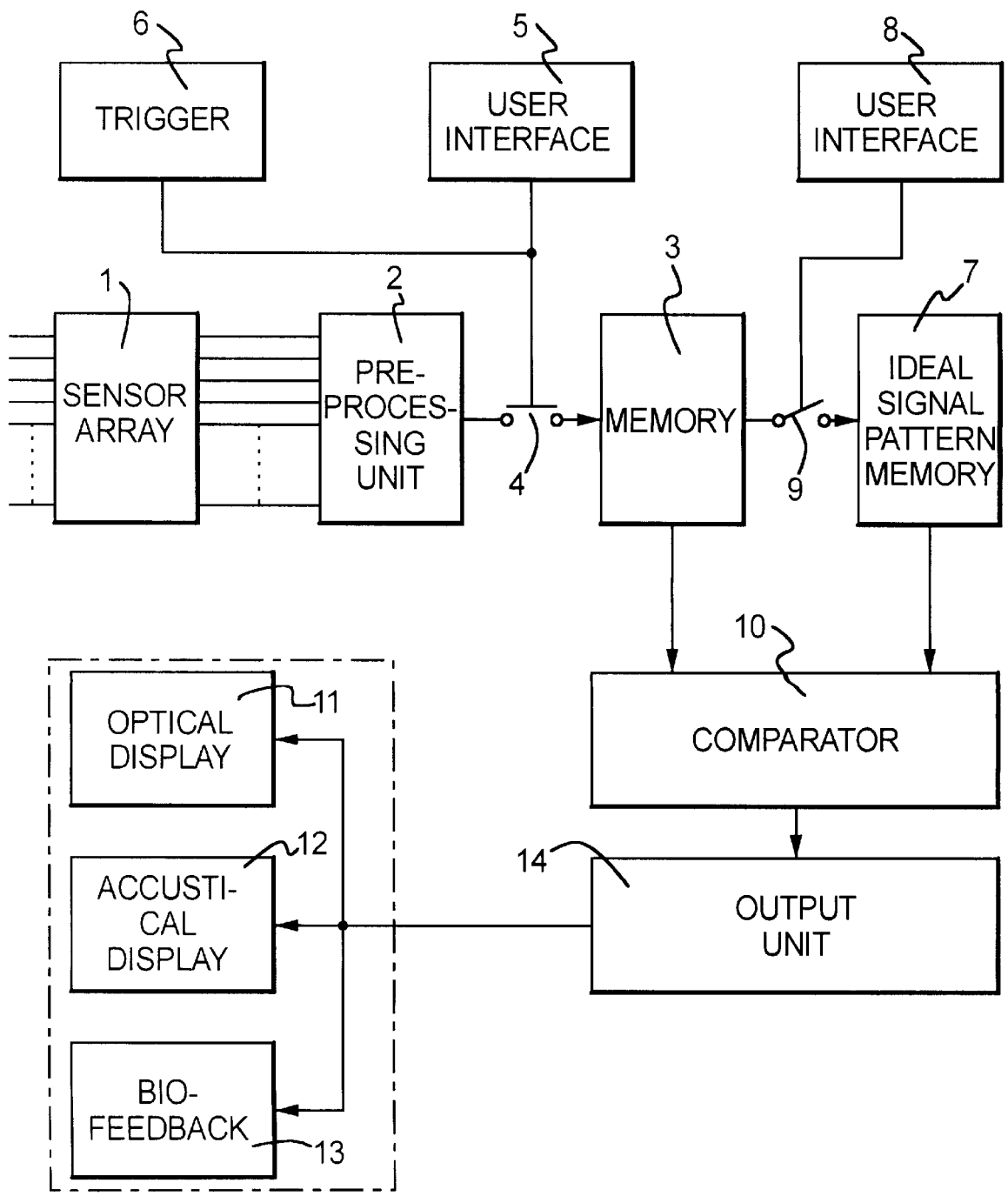

PATIENT MONITORING SYSTEM

BACKGROUND OF THE INVENTION

1. Field of the Invention

The present invention is directed to a patient monitoring system, and in particular to a system for monitoring an orthopedic patient.

2. Description of the Prior Art

Many orthopedic disturbances or diseases are caused or aggravated by improper movement sequences or postures (e.g. back problems). The prevention or therapy largely consists in the training of improved movement sequences or postures. It is essential for success to practice the corresponding movement sequences or postures correctly, since otherwise there may even occur a worsening of the health condition.

Today, movement or weight sequences are trained or corresponding exercises are learned under supervision (physical therapy). The exercises are then repeated at home without supervision.

German OS 40 39 648 teaches a measurement value processing system for a biological subject in which there are sensors for measurement values. The measurement values are mathematically evaluated and compared to predetermined measurement value structures. It is possible to trigger a storage means, a control means, or an alarm means depending on these measurement values. There are no teachings in this publication with respect to the design of the orthopedic monitoring or the capturing of movements of the subject. This also applies to the evaluation method for ECG signals which is described in German PS 32 09 850, in which ECG electrodes, which are not suitable for the direct capture of movements, are provided as sensors.

PCT Application WO 91/12786 teaches an orthopedic exercise device which comprises a housing that comprises two subportions which can be moved relative to each other. The subportions respectively comprise two opposite bars oriented parallel to each other, between which a body part can be placed. The two bars of the first subportion of the housing are connected to the two other bars of the second subportion via a hinge that can be adjusted with respect to its ability to move. For example, if a leg of a patient is inserted into the exercise device, the shin being clamped in one subportion of the housing and the thigh in the other, the patient can move the shin relative to the thigh in the framework of the freedom of motion which can be adjusted at the hinge. At the rods of the subportions of the exercise device, pressure sensors are arranged which measure forces of pressure on the rods of the exercise device that arise in exercises.

U.S. Pat. No. 5,538,486 teaches a therapy device which is provided for training and which comprises an extendible cord which is connected to a sensor arrangement. The sensor arrangement is allocated to a microprocessor control module which is accepted in a housing. The housing is connected to a handle which is provided for the actuation of the therapy device. For performing exercises, the free end of the extendible cord is fastened at a suitable device, so that a patient can perform strength exercises with the therapy device by pulling at the handle. Sensor signals are measured with the sensor arrangement which cooperates with the extendible cord, it being possible for the microprocessor to evaluate these signals, display them on a display as force values, store them in a memory, or to compare them to specified force values.

SUMMARY OF THE INVENTION

An object of the invention is to provide an orthopedic patient monitoring system which is suitable for use by a medical layman in a customary environment and which gives this person information about the performing of exercises.

The above object is achieved in accordance with the principles of the present invention in an orthopedic patient monitoring system having movement sensors for biomedical signals which measure compression forces and shearing forces and/or accelerations, a memory in which the sensor signals or processed sensor signals, are stored as a current signal pattern, a memory for storing an ideal signal pattern-derived from ideal motion sequences or postures specified by experts, and a comparator for comparing the contents of these two memories and a display for displaying a result of the comparison.

The inventive monitoring system is particularly suitable for checking movements and movement sequences given orthopedic disturbances or diseases.

With the aid of suitable sensors, compression and shearing forces (e.g. with piezoelectric films) and/or accelerations are measured. The measurement of the pressing and shearing forces can occur by means of sensors which are built into the soles of shoes, for example. Measurement values can correspond to both individual measurements and dynamic sequences. This can occur either in a training situation (regular exercises) or in the daily routine (e.g. checking of seated posture). The measurement values can either be evaluated directly in a unit worn at the body (transmission by cable or telemetry) or can be transmitted to a stationary unit by telemetry.

The measurement values are compared to predetermined stored ideal values. The ideal values are derived from ideal motion sequences or postures as specified by experts (physician or physical therapist). The input can thus occur by direct specification of defined patterns or values, by selection from a stored set of specifications or by training, i.e. by measurement and storage of a real situation (e.g. therapist's demonstration, exercise under supervision and storing of a successful exercise).

The evaluation of the measurement values can also occur in a self-learning manner (e.g. with neural networks), e.g. by the user producing an input to the device given an incorrect movement sequence or an incorrect posture (e.g. detectable by pain). The relevant data record accumulated over a predetermined time frame (e.g. the last 30 seconds) is stored. With the aid of the stored data records, the system learns to recognize undesirable conditions early and can give a prompt warning before pain is experienced, for example.

As a further possible additional function, the current measurement values can be stored (locally or in a database that is accessible by a network link) in order to enable a (later) evaluation by the experts (physician or physical therapist). A selective acknowledging message is delivered to the user indicating how well his current movement sequences or postures conform to the specified ideal values. To this end, the measurement values can be combined with expert knowledge (locally or by remote inquiry) in order to derive selective instructions for action, or for improvement. The acknowledging indication can occur by means of optical or acoustical signals, by stimulation of the pain or tactile sense (biofeedback) or by complex instructions for action. In particular, a telemetric transmission is possible from the evaluation unit to units worn on the body (such as a small earphone at the ear).

The basis of the invention is the combining of the above functions in a device for medical laymen, particularly the automatic evaluation of the measurements and the feedback to the user.

DESCRIPTION OF THE DRAWING

The single FIGURE is a schematic block diagram of a patient monitoring system constructed and operating in accordance with the principles of the present invention.

DESCRIPTION OF THE PREFERRED EMBODIMENTS

The drawing depicts a sensor array 1 (e.g. with pressure sensors in the sole of the shoe, muscle sensors, acceleration sensors on a moving body part) whose measurement values are fed to a signal preprocessing unit 2. The signal preprocessing unit 2, which preprocesses the measurement values of all the sensors, can contain filters, amplifiers, AD converters and means for signal linkage and parameter extraction, for example. The output signal of the signal preprocessing unit 2 can be fed to a memory 3 via a switch 4. In the memory 3, a first signal matrix of the preprocessed signals of all sensors in sensor array 1 within a predetermined time window T1–T2 is stored as the current signal pattern. The time window T1–T2 is specified by means of a user interface to which a trigger 6 is allocated for the activation and deactivation, the output signals of this trigger 6 being derived from current sensor signals.

A memory 7 for a second signal matrix embodying an ideal signal pattern is allocated to the memory 3. The ideal signal pattern can be determined during a training phase by the averaging of several signal patterns, for example. Storage of the ideal signal pattern is controlled by a user interface 8, which actuates a switch 9 for storing this ideal signal pattern when it is decided that the memory 7 contains such an ideal signal pattern.

A comparator 10 compares the contents of the memories 3 and 7 and delivers information about the comparison result via an output unit 14. This information can be communicated to the user or the patient via an optical display 11, an acoustical display 12 or a biofeedback 13. The biofeedback 13 can be the application of a stimulating current at muscle or nerve cells, for example.

Although modifications and changes may be suggested by those skilled in the art, it is the intention of the inventors to embody within the patent warranted hereon all changes and modifications as reasonably and properly come within the scope of their contribution to the art.

We claim as our invention:

1. An orthopedic patient monitoring system comprising:

a plurality of movement sensors for biomedical signals selected from the group of sensors comprising compression force sensors, shearing force sensors and acceleration sensors, said movement sensors respectively generating measurement signals;

a first memory containing a signal pattern derived from said measurement signals;

a second memory containing an idealized signal pattern obtained from measurement signals from said sensors under conditions for optimizing said measurement signals to produce said idealized signal pattern;

a comparator connected to said first memory and to said second memory for comparing the signal pattern stored in said first memory and the signal pattern stored in said second memory to obtain a comparison result; and an output unit for producing an output dependent on said comparison result.

2. An orthopedic monitoring system as claimed in claim 5 further comprising a user interface for storing said signal pattern in said second memory for selectively manually producing said signal pattern in said second memory.

3. An orthopedic monitoring system as claimed in claim 1 wherein said output unit comprises a biofeedback unit adapted to stimulate a person experiencing movements sensed by said movement sensors dependent on said comparison result.

4. An orthopedic monitoring system as claimed in claim 1 wherein said movement sensors are adapted to directly obtain said measurement signals from a subject.

5. An orthopedic monitoring system as claimed in claim 4 wherein said movement sensors are adapted to be arranged at an article of clothing of subject.

6. An orthopedic monitoring system as claimed in claim 4 wherein said movement sensors are adapted for attachment to a muscle of a subject.

7. An orthopedic monitoring system as claimed in claim 4 wherein said movement sensors are adapted for allocation to a moving body part of a subject.

* * * * *